US007973016B2

(12) United States Patent
Mathis et al.

(10) Patent No.: US 7,973,016 B2
(45) Date of Patent: Jul. 5, 2011

(54) METHODS OF TREATING, REDUCING, OR PREVENTING AUTOIMMUNE CONDITIONS

(75) Inventors: Diane Mathis, Brookline, MA (US); Christophe O. Benoist, Brookline, MA (US); Hsin-Jung Wu, Brookline, MA (US)

(73) Assignee: Joslin Diebetes Center, Boston, MA (US)

( * ) Notice: Subject to any disclaimer, the term of this patent is extended or adjusted under 35 U.S.C. 154(b) by 646 days.

(21) Appl. No.: 10/586,401

(22) PCT Filed: Jan. 24, 2005

(86) PCT No.: PCT/US2005/002097
§ 371 (c)(1),
(2), (4) Date: Jun. 4, 2007

(87) PCT Pub. No.: WO2005/072290
PCT Pub. Date: Aug. 11, 2005

(65) Prior Publication Data
US 2008/0020991 A1    Jan. 24, 2008

Related U.S. Application Data

(60) Provisional application No. 60/538,732, filed on Jan. 23, 2004.

(51) Int. Cl.
*C12N 15/11*    (2006.01)
*C07H 21/02*    (2006.01)
*C07H 21/04*    (2006.01)

(52) U.S. Cl. ..... 514/44; 536/23.1; 536/24.3; 536/24.33; 536/24.5

(58) Field of Classification Search ................. 536/23.1, 536/24.3, 24.33, 24.5; 514/44
See application file for complete search history.

(56) References Cited

U.S. PATENT DOCUMENTS

| 5,675,060 | A | 10/1997 | Benoist et al. |
| 6,194,388 | B1 | 2/2001 | Krieg et al. |
| 6,207,646 | B1 * | 3/2001 | Krieg et al. ................. 514/44 R |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,406,705 | B1 | 6/2002 | Davis et al. |
| 6,613,751 | B2 * | 9/2003 | Raz et al. ........................ 514/44 |
| 6,653,292 | B1 | 11/2003 | Krieg et al. |

(Continued)

FOREIGN PATENT DOCUMENTS
WO    WO 00/09159    2/2000

(Continued)

OTHER PUBLICATIONS

Wu et al. (Journal of Experimental Medicine, 2007 vol. 204, No. 8, published Jul. 23, 2007, pp. 1911-1922).*

(Continued)

*Primary Examiner* — Sean McGarry
*Assistant Examiner* — Terra Cotta Gibbs
(74) *Attorney, Agent, or Firm* — Clark & Elbing LLP

(57) ABSTRACT

The present invention relates to methods and kits for treating, reducing, or preventing autoimmune conditions such as rheumatoid arthritis by administering to a mammal in need thereof an agent that modulates the expression level or biological activity of Toll-like receptor-9 (TLR-9). Also disclosed are screening methods that make use of TLR-9 for the identification of novel therapeutics for autoimmune conditions.

26 Claims, 6 Drawing Sheets

U.S. PATENT DOCUMENTS

| | | | |
|---|---|---|---|
| 7,208,478 B2* | 4/2007 | Carson et al. | 514/44 |
| 7,271,156 B2* | 9/2007 | Krieg et al. | 514/44 |

FOREIGN PATENT DOCUMENTS

| | | |
|---|---|---|
| WO | WO 00/64469 | 11/2000 |

OTHER PUBLICATIONS

Ballas et al., "Divergent Therapeutic and Immunologic Effects of Oligodeoxynucleotides with Distinct CpG Motifs," *J. Immunol.* 167:4878-4886 (2001).

Chiang et al., "Ribavirin or CpG DNA Sequence-Modulated Dendritic Cells Decrease the IgE Level and Airway Inflammation," *Am. J. Respir. Crit. Care Med.* 168:575-580 (2003).

Choe et al., "Interleukin 1 Receptor Dependence of Serum Transferred Arthritis Can be Circumvented by Toll-Like Receptor 4 Signaling," *J. Exp. Med.* 197:537-542 (2003).

Daniliuc et al., "Hypoxia Inactivates Inducible Nitric Oxide Synthase in Mouse Macrophages by Disrupting its Interaction with Alpha-Actinin 4," *J. Immunol.* 171:3225-3232 (2003).

Deng and Tarkowski, "Synovial Cytokine mRNA Expression During Arthritis Triggered by CpG Motifs of Bacterial DNA," *Arthritis Res.* 3:48-53 (2001).

Deng et al., "Intra-Articularly Localized bacterial DNA containing CpG Motifs Induces Arthritis," *Nat. Med.* 5:702-705 (1999).

Gramzinski et al., "Interleukin-12- and Gamma Interferon-Dependent Protection Against Malaria Conferred by CpG Oligodeoxynucleotide in Mice," *Infect. Immun.* 69:1643-1649 (2001).

Hartung et al., "Th2-Mediated Atopic Disease Protection in Th1-Mediated Rheumatoid Arthritis," *Clin. Exp. Rheumatol.* 21:481-484 (2003).

Ji et al., "Critical Roles for Interleukin 1 and Tumor Necrosis Factor α in Antibody-Induced Arthritis," *J. Exp. Med.* 196:77-85 (2002).

Ji et al., "Genetic Influences on the End-Stage Effector Phase of Arthritis," *J. Exp. Med.* 194:321-330 (2001).

Korganow et al., "From Systemic T Cell Self-Reactivity to Organ-Specific Autoimmune Disease Via Immunoglobulins," *Immunity* 10:451-461 (1999).

Kouskoff et al., "Organ-Specific Disease Provoked by Systemic Autoimmunity," *Cell* 87:811-822 (1996).

Krieg, "CpG Motifs in Bacterial DNA and Their Immune Effects," *Annu. Rev. Immunol.* 20:709-760 (2002).

Shirota et al., "B Cells Capturing Antigen Conjugated with CpG Oligodeoxynucleotides Induce Th1 Cells by Elaborating IL-12," *J. Immunol.* 169:787-794 (2002).

International Search Report for PCT/US2005/02097 dated Jun. 9, 2006.

International Preliminary Report on Patentability for PCT/US2005/02097 dated Aug. 29, 2006.

* cited by examiner

METHODS OF TREATING, REDUCING, OR PREVENTING AUTOIMMUNE CONDITIONS

CROSS REFERENCE TO RELATED APPLICATIONS

This application is the U.S. National Stage of International Application No. PCT/US2005/002097, filed Jan. 24, 2005, which claims benefit of U.S. Provisional Application No. 60/538,732, filed Jan. 23, 2004, hereby incorporated by reference.

INCORPORATION BY REFERENCE OF A SEQUENCE LISTING FILED ELECTRONICALLY

Kindly incorporate the .txt file Sequence Listing, submitted Feb. 10, 2011, having the name 50339_002002_ST25.txt, file size 1.28 KB, created on Feb. 2, 2011.

BACKGROUND OF THE INVENTION

In general, the present invention features methods of treating, reducing, or preventing autoimmune conditions, such as rheumatoid arthritis. Also disclosed are screening methods for identifying candidate compounds useful to treat, reduce, or prevent autoimmune conditions.

The immune system protects the body from potentially harmful agents such as microorganisms, cancer cells, and toxins. The body's ability to recognize foreign or 'non-self' entities or antigens results in the production of antibodies and in the sensitization of immune cells, ultimately culminating in the destruction of foreign agents.

Immune system disorders or autoimmune conditions arise when the immune system no longer differentiates self and non-self antigens and aberrantly mounts an immune response against self-antigens, thereby resulting in the destruction of host cells, tissues, or organs. Rheumatoid arthritis (RA) is one such disease, characterized by the slow erosion of the cartilage and bones. A large proportion of arthritic patients run a course of intermittent relapses and remissions with an overall pattern of slowly progressive joint destruction and deformity. Clinical manifestations include symmetrical polyarthritis of peripheral joints associated with pain, tenderness, swelling, and loss of function of affected joints; morning stiffness; loss of cartilage; erosion of bone matter; and subluxation of joints after persistent inflammation. This condition also manifests itself extra-articularly, causing rheumatoid nodules, rheumatoid vasculitis, pleuro-pulmonary inflammation, scleritis, sicca syndrome, Felty's syndrome (splenomegaly and neutropenia), osteoporosis, and weight loss (Katz *Am. J. Med.*, (1985) 79:24 and Krane and Simon, *Advances in Rheumatology*, Synderman (ed.), (1986) 70(2):263-284). In some cases, arthritis may even be associated with mortality.

Autoimmune conditions are typically chronic in nature, requiring lifelong care and monitoring. Currently, most available treatment modalities are suboptimal and few autoimmune diseases can actually be cured. Medications or therapies that slow or suppress the immune system response in an attempt to halt the inflammation associated with the autoimmune response are often used. Unfortunately, these medications also suppress the ability of the immune system to fight infection and are therefore associated with various serious side effects. In the case of RA, various therapeutic strategies, including the administration of NSAIDs for example, may temporarily relieve arthritic symptoms. These strategies however, are often associated with limited efficacy and serious debilitating side effects.

Thus, better treatment modalities are required to treat, prevent, or reduce autoimmune conditions.

SUMMARY OF THE INVENTION

In general, the present invention is based on our discovery that the administration of agents that modulate the expression level or biological activity of the Toll-like receptor-9 (TLR-9) results in the treatment, prevention, or reduction of autoimmune conditions, such as rheumatoid arthritis. Exemplary agents include unmethylated CpG oligonucleotides (CpG ODNs).

Accordingly, in a first aspect, the invention features a method of treating, reducing, or preventing an autoimmune condition by administering to a mammal (e.g., a human, pet, or domestic farm animal) a therapeutically effective amount of a pharmaceutical composition containing an agent that modulates the expression level or biological activity of the Toll-like receptor-9 (TLR-9). For example, the composition may contain a nucleic acid molecule having the sequence GACGTT (SEQ ID NO: 1) or GTCGTT (SEQ ID NO: 2). Exemplary nucleic acid molecules may therefore contain the sequences 5' TCC ATG ACG TTC CTG ACG TT 3' (SEQ ID NO: 3) or 5' TCT CCC AGC GTG CGC CAT 3' (SEQ ID NO: 4). Desirably, the nucleic acid molecule contains at least one, two, three, or more than three unmethylated CpG dinucleotides (CpG ODNs). The nucleic acid of the invention may be single-stranded or double-stranded and may be DNA or RNA. Further, the nucleic acid molecule of the invention may modulate the activity of B cells, dendritic cells, monocytes, macrophages, or combinations thereof. Alternatively, the nucleic acid molecule may modulate the levels of TNF-α, IL-12, or other soluble mediators. Autoimmune conditions amenable to treatment include, without limitation, inflammatory arthritis (e.g., rheumatoid arthritis, juvenile arthritis, or psoriatic arthritis), inflammatory bowel disease, multiple sclerosis, myasthenia gravis, diabetes type I, or systemic lupus erythematosus (SLE).

Optionally, the nucleic acid molecule may also contain a phosphate backbone modification, such as a phosphothiorate or a phorphorodithioate modification either on the 5' or 3' inter-nucleotide linkages. Although the nucleic acid molecule may be of any size, desirably its size ranges between 8 to 100 nucleotides and more preferably between 8 to 30 nucleotides.

Desirably, the pharmaceutical composition is administered systemically to the mammal being treated. Optionally, the mammal is also administered a second therapeutic regimen, such as immunosuppressants, NSAIDs, COX-2 inhibitors, biologics, non-steroidal calcineurin inhibitors, steroidal anti-inflammatory agents (e.g., beclomethasone, flunisolide, budesonide, triamcinolone, prednisolone, dexamethasone, fluticasone, meclofenamate sodium, meloxicam, oxaprozin, sulindac, and tolmetin), 5-amino salicylic acid, DMARDs, hydroxychloroquine sulfate, inflammatory modulators (e.g., agents that modulate the expression of inflammatory cytokines (e.g., TNF-α or IL-1) or their receptors), agents that interfere with B cell action (e.g., anti-CD20 antibodies such as rituximab), or penicillamine.

In a related aspect, the invention features kits that include any pharmaceutical composition of the invention in combination with instructions for administering the composition to treat, prevent, or reduce an autoimmune condition, such as rheumatoid arthritis.

In another aspect, the invention provides methods for identifying a candidate compound for treating, reducing, or preventing an autoimmune condition in a mammal. These methods involve the steps of: (a) contacting a cell expressing a TLR-9 gene with a candidate compound; and (b) measuring TLR-9 gene expression or TLR-9 protein activity in the cell. A candidate compound that modulates the expression or the activity of TLR-9, relative to TLR-9 expression or activity in a cell not contacted with the candidate compound, is identified as a candidate compound useful for treating, reducing, or preventing an autoimmune condition in a mammal.

In preferred embodiments, the TLR-9 gene is a TLR-9 fusion gene and the TLR-9-expressing cell is a mammalian cell (e.g., a rodent cell). The cell may be an immune cell, such as a B cell, dendritic cell, monocyte, or macrophage. In other embodiments, step (b) involves the measurement of TLR-9 mRNA or protein.

In a related aspect, the invention provides methods for identifying a candidate compound for treating, reducing, or preventing an autoimmune condition in a mammal. These methods involve the steps of: (a) contacting a TLR-9 protein with a candidate compound; and (b) determining whether the candidate compound binds the TLR-9 protein and/or modulates TLR-9 activity. Candidate compounds that bind and modulate TLR-9 activity are identified as candidate compounds useful for treating, reducing, or preventing an autoimmune condition, in a mammal.

By "autoimmune condition" is meant any condition in which the immune system of a host develops an immune response against host antigens, resulting in the destruction of self-tissues, organs, or cells. Such conditions include, for example, inflammatory arthritis (e.g., psoriatic arthritis, juvenile arthritis, or rheumatoid arthritis), inflammatory bowel disease, multiple sclerosis, myasthenia gravis, diabetes type I, or systemic lupus erythematosus (SLE). Asthma is particularly excluded from the definition of an autoimmune condition.

By "treating, reducing, or preventing an autoimmune condition" is meant ameliorating such condition, its associated symptoms, or both before or after it has occurred. As compared with an equivalent untreated control, such reduction or degree of prevention is at least 5%, 10%, 20%, 40%, 50%, 60%, 80%, 90%, 95%, or 100% as measured by any standard technique. Typically, a patient who is being treated for an autoimmune condition is one who a medical practitioner has diagnosed as having such a condition. Diagnosis may be performed by any suitable means known in the art or as described herein Typically, autoimmune conditions are diagnosed by the evaluation of symptoms, or alternatively, by the detection of autoantibodies or self-reactive immune cells. The diagnosis will depend on the nature of the autoimmune condition and will be performed using any standard method known in the art or any method described herein.

The antinuclear antibody test (ANA) or fluorescent antinuclear antibody (FANA) test, for example, may be used to detect SLE, scleroderma, Sjögren's syndrome, Raynaud's disease, juvenile chronic arthritis, rheumatoid arthritis, antiphospholipid antibody syndrome, autoimmune hepatitis, and other autoimmune disorders. The C-reactive protein test may also be used to detect inflammation-associated autoimmune conditions.

Rheumatoid arthritis (RA) is typically diagnosed based on the overall pattern of symptoms, medical history, physical examination, X-rays, and laboratory tests including tests that detect rheumatoid factor (i.e. the Latex test) or other autoantibodies. Rheumatoid factor is an antibody found in the blood of about 80% of adults with RA. While X-rays cannot confirm the presence of rheumatoid arthritis, they may be used to rule out other diseases. X-rays may also establish a baseline for comparison as the disease progresses. The presence of active inflammation in the mammal may also be determined using a sedimentation rate test. In this test, blood is drawn and allowed to settle over a period of time. A high or increasing sedimentation rate in the blood indicates active inflammation. A follow-up test may determine whether inflammation is increasing or decreasing and whether additional treatment is needed.

A patient in whom the development of an autoimmune condition is being prevented may or may not have received such a diagnosis. One skilled in the art will understand that these patients may have been subjected to the same standard tests as described above (e.g., X-rays) or may have been identified, without examination, as one at high risk due to the presence of one or more risk factors (e.g., family history).

By "an effective amount" is meant an amount of a compound, alone or in a combination, required to treat, reduce, or prevent an autoimmune condition, its associated symptoms, or both in a mammal. The effective amount of active compound(s) varies depending upon the route of administration, age, body weight, and general health of the subject. Ultimately, the attending physician or veterinarian will decide the appropriate amount and dosage regimen.

By "modulate the level or activity of TLR-9" is meant to reduce or increase the expression level or the biological activity of TLR-9 relative to the expression level or biological activity of TLR-9 in an untreated control. According to this invention, such level or activity is modulated by at least 10%, 20%, 30%, 40%, 50%, 60%, 70%, 80%, 90%, 100%, or even greater than 100%, relative to an untreated control. Desirably, autoimmune conditions are treated, prevented, or reduced if the biological activity or level of TLR-9 is modulated in a mammal.

By "CpG" or "CpG motif" or "CpG dinucleotide" or "CpG oligonucleotide" is meant a nucleic acid having at least one occurrence of a cytosine followed by a guanine linked by a phosphate bond. The term "methylated CpG" refers to a CpG motif in which the cytosine on the pyrimidine ring (usually at the position 5 of the pyrimidine ring) is methylated. The term "unmethylated CpG" refers to a CpG motif characterized by the absence of methylation on the cytosine on the pyrimidine ring. According to this invention, methylation or the partial or entire removal of an unmethylated CpG motif in a nucleic acid molecule of the invention reduces its effect. The effect of methylation or removal of a CpG motif is "substantial" if the effect is similar to that of a nucleic acid that does not contain a CpG motif.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, antibodies, and components and derivatives thereof. Useful candidate compounds according to this invention modulate the biological activity of TLR-9, the expression level of TLR-9, or both.

By "TLR-9 fusion gene" is meant a TLR-9 promoter and/or all or part of a TLR-9 coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and β-galactosidase.

By "nucleic acid molecule" is meant multiple nucleotides, each of which contains a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G). As used herein, the term refers to oligoribonucleotides as well as oligodeoxyribonucleotides. The nucleic acid molecules of the invention also include polynucleosides (i.e. a polynucleotide lacking the phosphate) and any other organic base-containing polymer. Nucleic acid molecules may be obtained from existing nucleic acid sources (e.g. genomic or cDNA), but are desirably synthetic (e.g. produced by oligonucleotide synthesis).

By "nucleic acid delivery complex" is meant a nucleic acid molecule associated with (e.g. ionically, covalently bound to, or encapsulated within) a targeting means (e.g. a molecule that results in higher affinity binding to target cell (e.g. B-cell and natural killer (NK) cell) surfaces and/or that results in increased cellular uptake by target cells). Examples of nucleic acid delivery complexes include nucleic acids associated with a sterol (e.g. cholesterol), a lipid (e.g. a cationic lipid, virosome, or liposome), or a target cell-specific binding agent (e.g. a ligand recognized by target cell specific receptor). Preferred complexes are sufficiently stable in vivo to prevent significant uncoupling prior to internalization by the target cell. Desirably, the complex is cleaved under appropriate conditions within the cell, therefore releasing the nucleic acid in a functional form.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20$^{th}$ edition, (ed. A R Gennaro), Mack Publishing Co., Easton, Pa., 2000.

DETAILED DESCRIPTION

Figure 1:
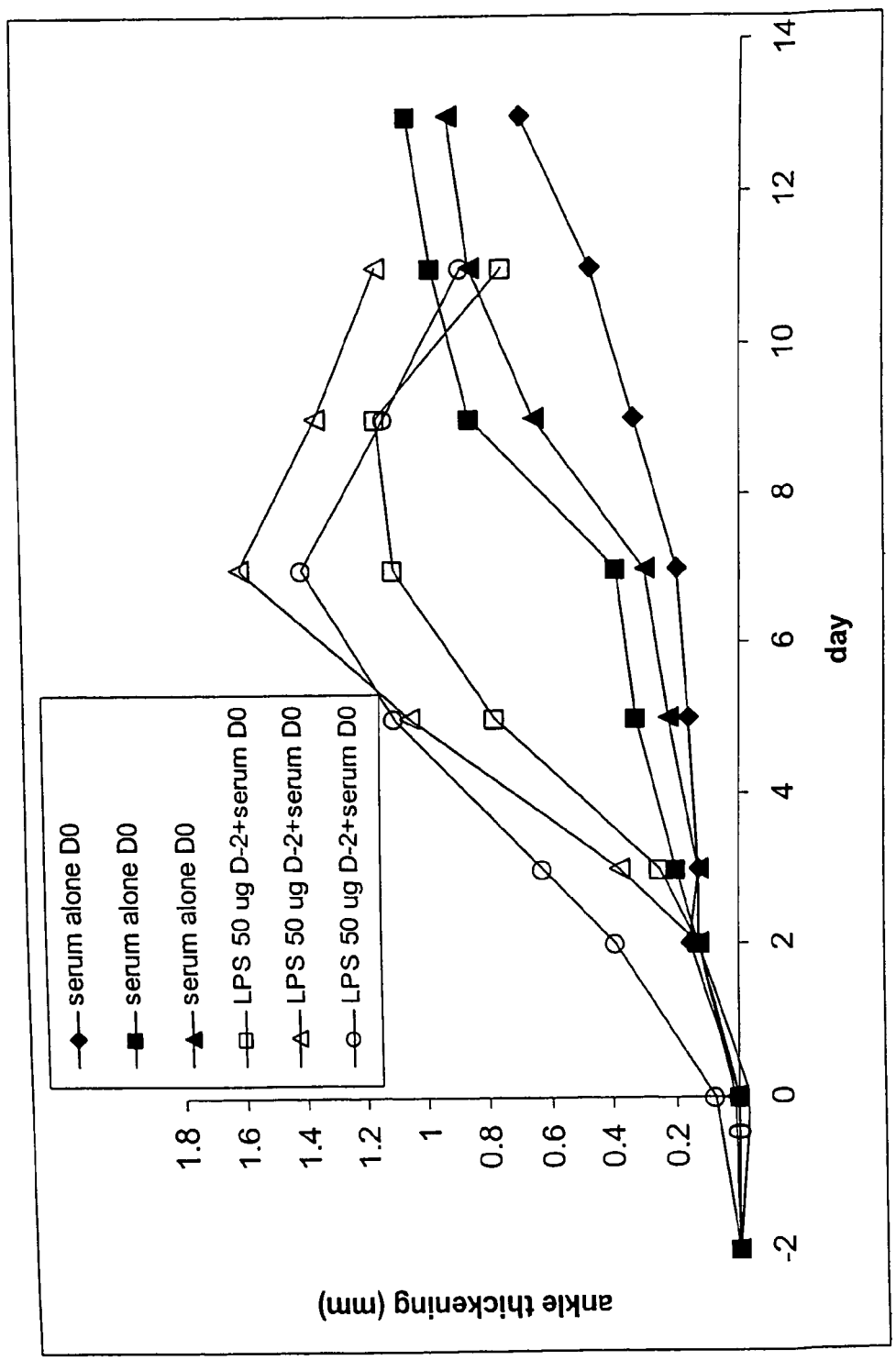
FIG. 1 is a graph showing the effect of LPS on ankle thickening as a function of time in the K/BxN model of arthritis.

The innate immune response is the first line of host defense against pathogens. Innate immune cells, such as dendritic cells, are first activated and subsequently trigger the generation of optimal adaptive immune responses. Although these cells lack the highly specific antigen receptors of B cells and T cells, they rely on a set of pattern recognition receptors (PRRs), which detect certain molecular structures present in pathogens. The innate immune system therefore detects pathogens by recognizing conserved motifs present in pathogen-associated components termed "pathogen-associated molecular patterns" (PAMPs) and in turn, activates the appropriate defense pathway.

Toll-like receptors (TLRs) are one class of PRRs that recognize PAMPs. To date, ten TLRs have been discovered (TLR1-10), each of which recognizes different ligands: TLR-4 recognizes lipopolysaccharide (LPS), TLR-2 recognizes peptidoglycan (PGN), TLR-3 recognizes double-stranded RNA (dsRNA), and TLR-9 recognizes unmethylated CpG motifs (CpG). Unmethylated CpG dinucleotides are prevalent in bacterial and viral DNAs, but are suppressed and methylated in vertebrate genomes. The immune system, including plasmacytoid dendritic cells (PDCs) and B cells, responds to the various CpG motifs by activating potent Th1-like immune responses (e.g., production of proinflammatory cytokines, interferons, and chemokines and activation of NK cells and B cells). Typically, CpG motifs having different backbones and different sequence motifs are associated with different profiles and kinetics of immune activation.

Autoimmune conditions arise when the immune system of a host fails to differentiate 'self'-antigens from foreign antigens such that an immune response is mounted against host organs, tissues, or cells ultimately resulting in self-destruction. The present invention is based on our discovery that unmethylated CpG oligonucleotides are effective in treating autoimmune conditions, likely through modulation of toll-like receptors (TLRs).

In particular, our results demonstrate that modulation of TLR-9 level or activity affects the onset and progression of autoimmune conditions. Using our K/BxN serum transfer model, we have shown that administration of nucleic acids containing unmethylated CpG ODN prevents the onset of arthritis and significantly reduces the severity of arthritis. In particular, the systemic administration of such oligonucleotides, such as ODN 1668 or ODN 1758, each of which have the ability to modulate the activity of TLR-9, was effective in preventing and reducing arthritis. Our results are surprising and unexpected as the intra-articular administration of ODN 1668 (5' TCC ATG ACG TTC CTG ATG CT 3'; SEQ ID NO:5) in particular had previously been shown to induce arthritis in various mouse models (Deng et al., (1999) Nature Medicine 5:702). The surprising nature of our findings is further emphasized by reports showing that stimulation of the TLR-4 enhances arthritis (Choe et al., (2003) *J. Exp. Med.* 197: 537-542).

Animal Models of Arthritis

Several animal models have been developed to study the pathogenesis of RA. There are several spontaneous mouse models that recapitulate features of human RA, including the MRL-lpr/lpr mouse, the New Zealand Black (NZB) mouse, the twy mouse, and the Sakaguchi (SKG) mouse. Various reagents can also induce arthritis, including type II collagen, antigen with Complete Freund's Adjuvant (CFA), CFA alone, streptococcal cell walls, proteoglycan, pristine, muramyl dipeptide, and Zymosan. Arthritis models have also been developed by genetic modification. Some genetic modifications induce arthritis by promoting a pro-inflammatory cytokine environment. These models include the human TNF-α transgenic mouse, the human IL-1α transgenic mouse, the BALB/c IL-1Rα-deficient mouse, and the mutant IL-6 receptor mouse.

We have developed a model of arthritis by crossing the K/RN T cell receptor (TCR) transgenic (Tg) mouse onto a C57B1/6xNOD F1 background (K/BxN). The resulting mouse model spontaneously develops a disease at 3-5 weeks of age with manifestations similar to human rheumatoid arthritis (Kouskoff et al., *Cell* (1996) 878:811). KRN Tg T cells are reactive to a self-peptide derived from glucose-6-phosphate isomerase (GPI), presented by the MHC class II molecule Ag[7]. Activated KRN T cells in turn activate B cells, which generate anti-GPI autoantibodies and mediate arthritis. In our model, the arthritic disease is critically dependent on both T and B cells. As in patients, the articular disorder in the K/BxN mouse is chronic, progressive, symmetrical, and has a proximal to distal gradient of severity. The histopathology of the K/BxN joint resembles that of human RA patients, and includes leukocyte infiltration, synovial hyperplasia, pannus formation, cartilage and bone destruction, and anarchic remodeling. The joints of K/BxN mice produce increased amounts of pro-inflammatory cytokines such as IL-1, TNF-α and IL-6 (Ji et al., *J. Exp. Med.* (2002) 196: 77). As in the case of human RA, K/BxN mice exhibit hypergammaglobulinemia and autoantibody production. However, in contrast to the majority of human RA patients, K/BxN mice do not develop RF. This arthritis model is described in detail in U.S. Pat. No. 5,675,060, hereby incorporated by reference.

Transfer of serum from arthritic K/BxN mice into non-transgenic mice induces arthritis in recipient mice in a highly reproducible and synchronized fashion (Korganow et al. *Immunity* (1999) 10: 451). Genetic effects on disease can be quickly assayed in this model by adoptive transfer of K/BxN serum into mice of various genetic backgrounds (Ji et al., *J. Exp. Med.* (2001) 194: 321). Because RA is a complicated multifactorial disease, this serum transfer model has allowed us to focus on the effector phase of RA and dissect the distal pathogenic mechanisms of disease.

The induction of arthritis by K/BxN serum transfer was performed as follows and as described in PCT WO 00/64469 hereby incorporated by reference. Sera from K/BxN mice (40 to 60 days of age) were pooled and two doses of 100-150 µl serum each were injected intraperitoneally (i.p.) at a two-day interval. We performed at least two repeats of each experiment, each of which included 3-5 mice.

Evaluation of arthritis was carried out for 14 days after serum transfer. The arthritis scoring system was as follows: (per paw) 0=no inflammation; 1=subtle inflammation; 2=easily identified swelling; 3=swelling on all aspects of the paw. Thus, the maximum score per mouse was 12. Ankle thickness was measured using a caliper, with ankle thickening being defined as the difference in ankle thickness from the day 0 measure.

CpG ODN 1668 Inhibits the Onset and Reduces the Severity of Serum-Induced Arthritis In order to test the effect of LPS on the severity of arthritis, a sub-optimal dose of serum (one dose of 100 µl serum) and recipients of a moderately susceptible strain (C57B1/6) were used. 50 µg of LPS was injected i.p. two days before serum transfer. (The administration protocol of 50 µg LPS i.p. on day −2 and 100 µl of serum on day 0 will be abbreviated as LPS+serum hereafter).

As shown in FIG. 1, LPS administered at a dose of 50 µg clearly increased the serum induced-ankle thickness and arthritis scores compared with the control group. However, injection of LPS (50 µg) alone did not induce arthritis. As expected, injection of LPS two days before serum administration enhanced arthritis development suggesting that LPS might work directly by recruiting inflammatory cells and increasing immune complexes to joints.

Figure 2:
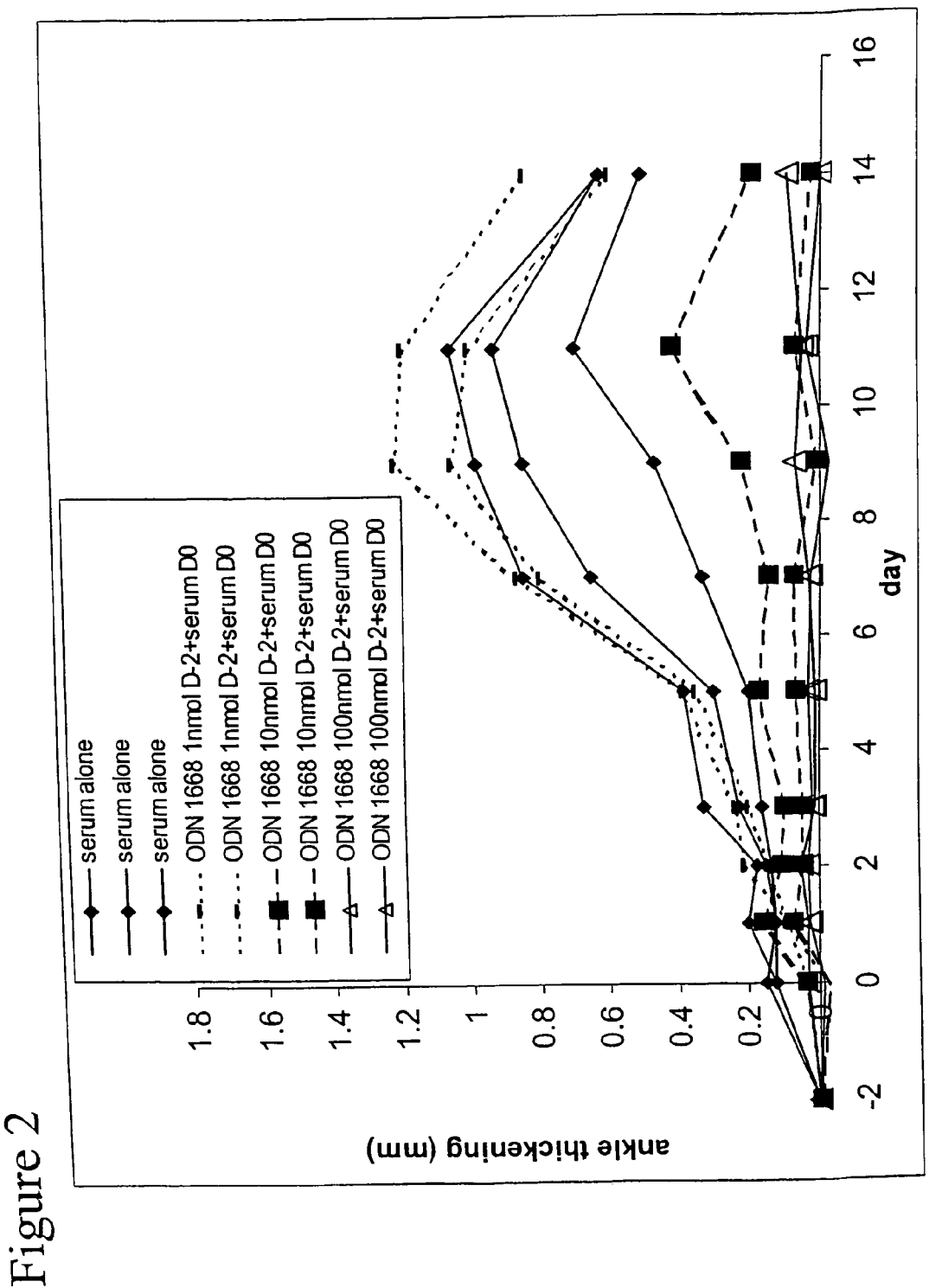
FIG. 2 is a graph showing the dose-dependent effect of CpG ODN 1668 on ankle thickening as a function of time in the K/BxN model of arthritis.
Figure 3:
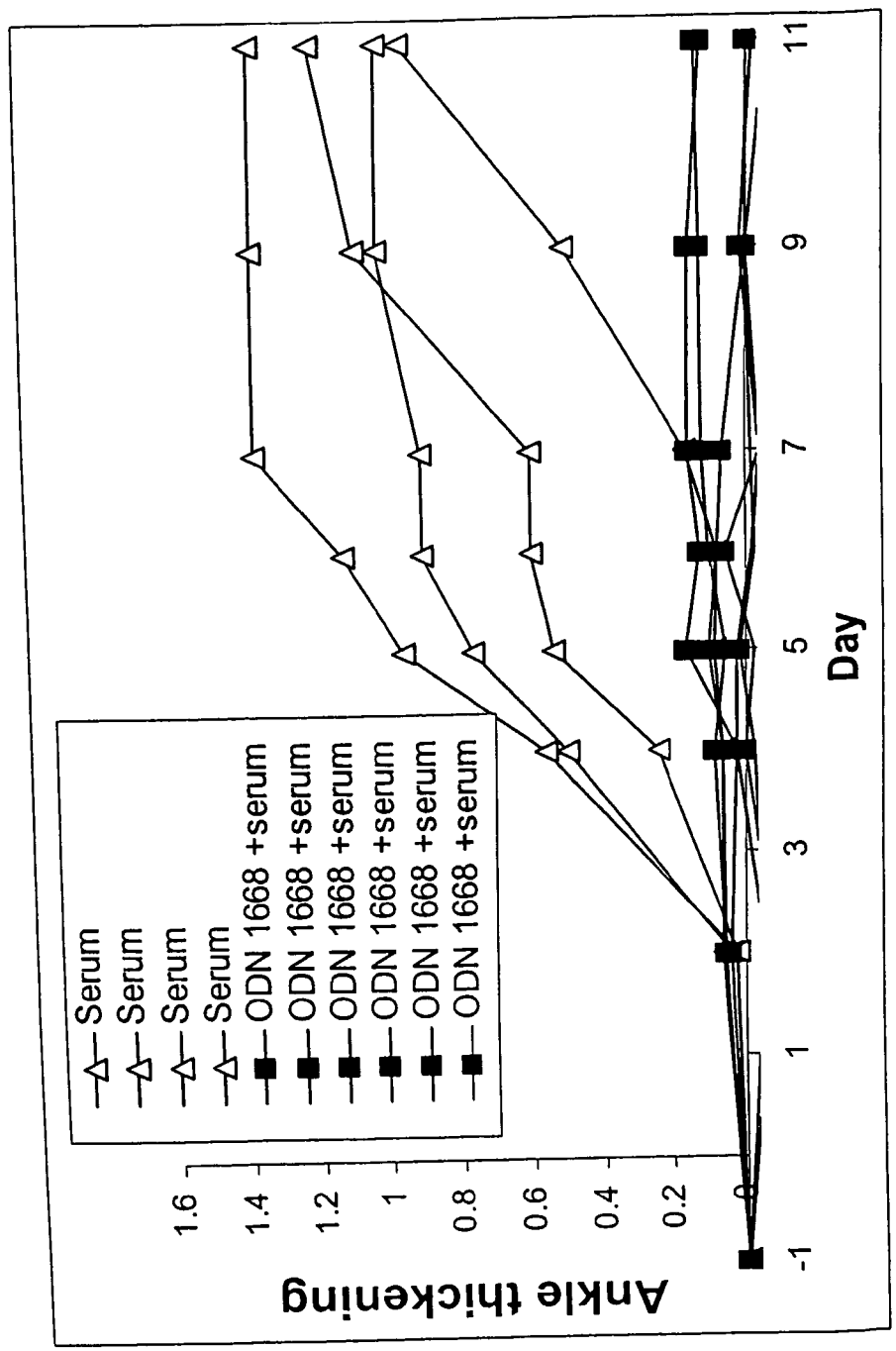
FIG. 3 is a graph showing the effect of CpG ODN 1668 on the onset of arthritis as a measure of ankle thickening in the K/BxN model of arthritis.
Figure 4:
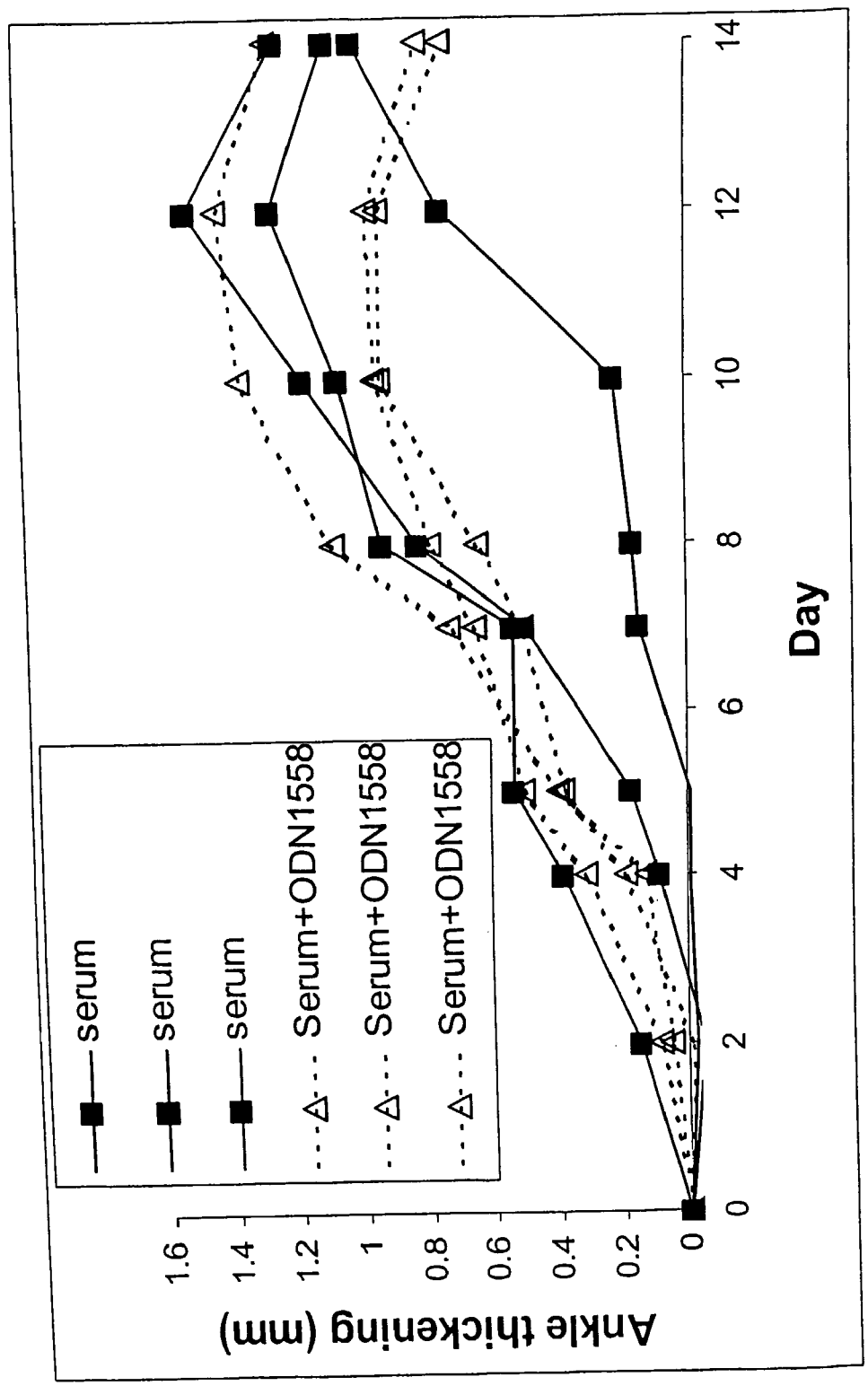
FIG. 4 is a graph showing the effect of CpG ODN 1585 on the onset of arthritis as a measure of ankle thickening in the K/BxN model of arthritis.
Figure 5:
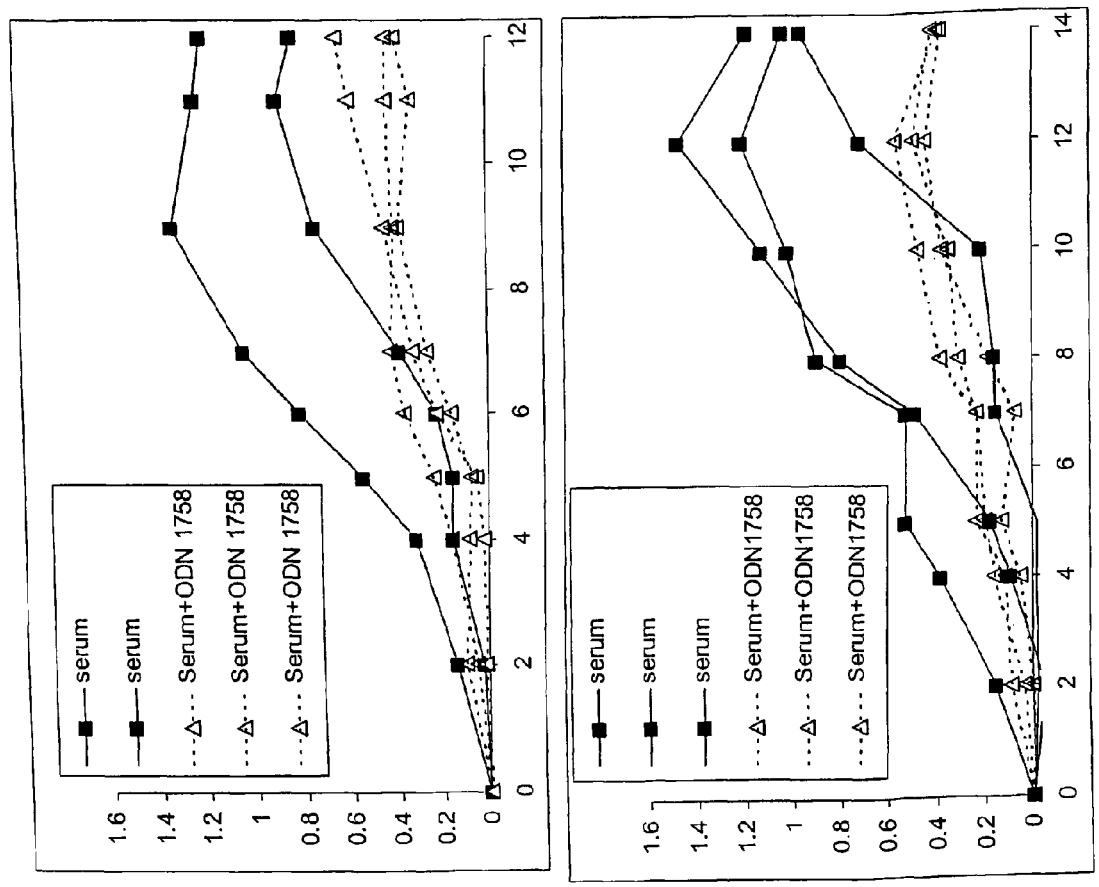
FIG. 5 is a series of graphs showing the effect of CpG ODN 1758 on the onset of arthritis as a measure of ankle thickening in the K/BxN model of arthritis.
Figure 6:
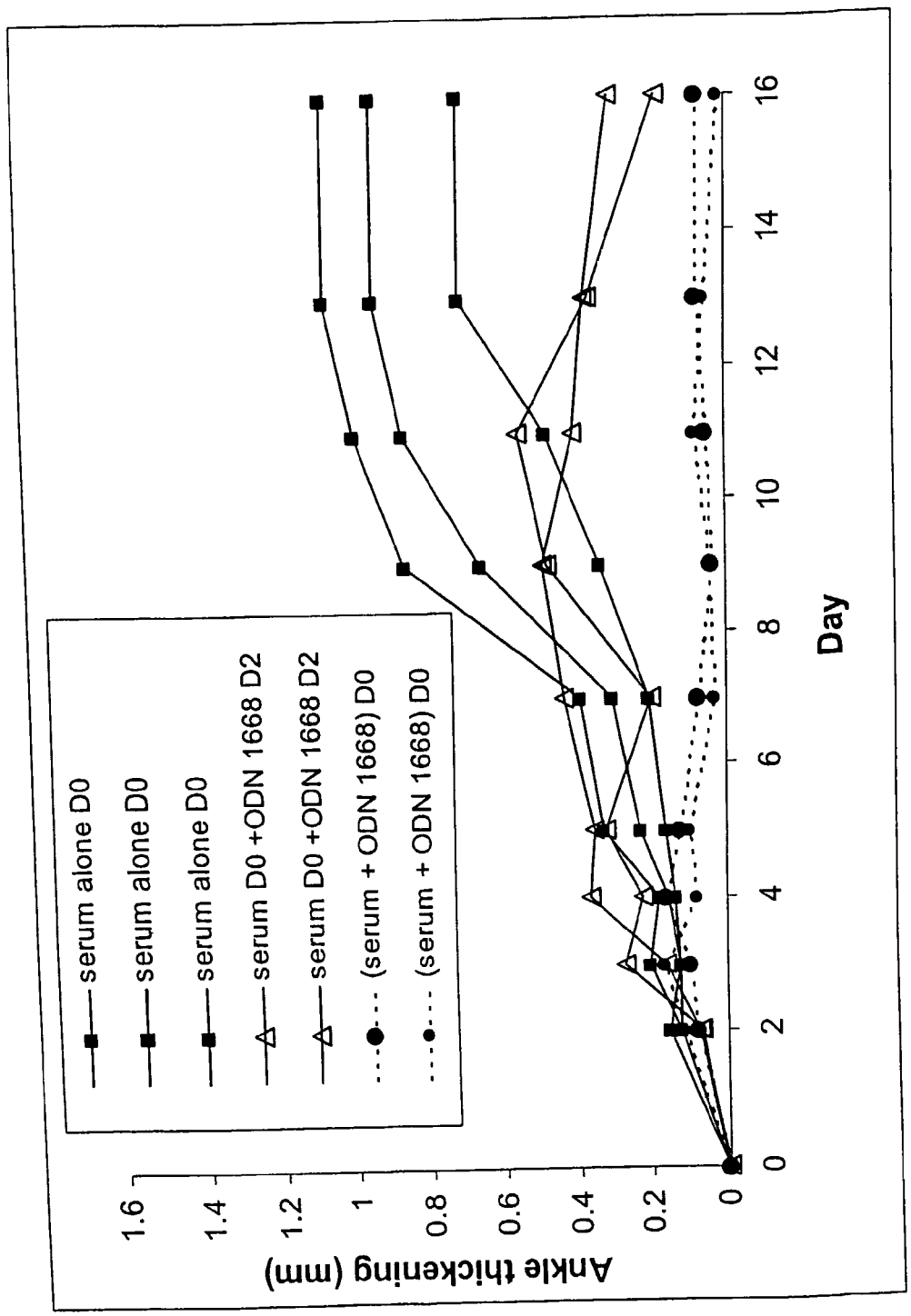
FIG. 6 is a graph showing the effect of CpG ODN 1668 on the progression of arthritis as a measure of ankle thickening in the K/BxN model of arthritis.

We next assessed the effect of unmethylated CpG ODN administration on the onset and progression of arthritis. ODN 1668 activates B cells, dendritic cells, monocytes, and macrophages and induces large amounts of TNF-α, IL-12, and other soluble mediators. ODN 1585, on the other hand, has negligible effect on B cell, TNF-α, and IL-12 stimulation, but is extremely efficient in the induction of natural killer cells to elicit target cell lysis and IFN production. Various doses of CpG ODN 1668 and ODN 1585 (1, 10, 100 nM) were administered i.p. either two days earlier, on the same day, or two days after serum transfer. While ODN 1585 (FIG. 4) has no effect on the onset or the progression of arthritis, ODN 1668 administered systemically could surprisingly prevent the onset of arthritis (FIG. 3) and significantly decrease the severity of arthritis (FIG. 6), which was initiated two days before injection by means of serum transfer. Furthermore, the administration of ODN 1758 (containing the sequence 5' TCT CCC AGC GTG CGC CAT 3' (SEQ ID NO: 4)) could also significantly delay the onset of arthritis (FIG. 5). Thus, the anti-arthritic effects of CpG-containing nucleic acid molecules were specific to particular CpG sequences. We also showed that this anti-arthritic effect was dose-dependent (see FIG. 2).

Overall, our findings are surprising since the administration of LPS and the stimulation of the TLR-4 have both had been previously shown to enhance arthritis. Our results were also unexpected given that the intra-articular administration of ODN 1668 had previously been shown to have the opposite effect (Deng et al., supra). Indeed, Deng and colleagues had previously shown that the intra-articular injection of unmethylated CpG motifs into the knee joints of mice, including ODN 1668, was sufficient to promote the onset of arthritis.

Pharmaceutical Compositions

Therapeutic Agents

Based on our discovery, the present invention provides methods for treating, preventing, or reducing autoimmune conditions by administering to a mammal (e.g., human) in need thereof a pharmaceutical composition containing an agent that modulates the expression level or the biological activity of TLR-9, including, for example, unmethylated CpG oligonucleotides. Useful agents according to the present invention may also include agents that indirectly modulate the expression level or biological activity of TLR-9 by modulating the expression level or biological activity of any of the signaling molecules involved in the TLR-9 signaling pathway.

Autoimmune conditions particularly amenable to treatment include, for example, inflammatory arthritis (e.g., rheumatoid arthritis, juvenile arthritis, psoriatic arthritis), multiple sclerosis, inflammatory bowel disease, myasthenia gravis, diabetes type I, or systemic lupus erythematosus (SLE). Desirably, the pharmaceutical composition contains an agent that exhibits an anti-autoimmune (e.g., anti-arthritic) effect that is at least 10%, 20%, 30%, 40%, 50%, 60%, 70%, 80%, 90%, 95%, 100%, or more that that exhibited by ODN 1668.

Nucleic acid molecules useful for the present invention include, for example, nucleic acid molecules that contain CpG ODNs (i.e., a 5' cytosine followed by 3' guanosine linked by a phosphate bond) and that have the sequence 5' GAC GTT 3' (SEQ ID NO: 1) or 5' GTC GTT 3' (SEQ ID NO: 2). For example, the nucleic acid molecule may contain the sequence 5' TCC ATG ACG TTC CTG ACG TT 3' (SEQ ID NO: 3) or 5' TCT CCC AGC GTG CGC CAT 3' (SEQ ID NO: 4). Desirably, the nucleic acid of the invention contains at least one, two, three, or more than three unmethylated CpG ODNs.

The nucleic acid molecule of the invention may be DNA or RNA and may be single-stranded or double-stranded. In general, double-stranded molecules are more stable in vivo, while single stranded molecules have increased immunomodulatory activity.

Desirably, the size of the immunomodulatory CpG-containing nucleic acid ranges between 8 to 30 bases to facilate uptake into cells. However, nucleic acids of any size (even many kb long) are useful according to the invention if sufficient immunomodulatory motifs are present, since such larger nucleic acids are typically degraded into oligonucleotides inside of cells. For example, CpG-containing nucleic acids may be produced on a large scale in plasmids, which are subsequently degraded into oligonucleotides upon administration to the mammal being treated.

Prolonged immunomodulation may be achieved using stabilized nucleic acid molecules. In this regard, the nucleic acid of the invention may be modified to increase their resistance to in vivo degradation. For example, modification of the nucleic acid backbone may enhance the immunomodulatory activity of the CpG oligonucleotides in vivo due to enhanced nuclease resistance, increased cellular uptake, increased protein binding, and/or altered intracellular localization. Other exemplary modified nucleic acid molecules include phosphothiorate modified oligonucleotides, phosphodiester modified oligonucleotides, combinations of phosphodiester and phosphorothioate oligonucleotides, methylphosphonate, methylphosphorothioate, phosphorodithiaoate, and combinations thereof.

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acid moleules which contain diol, such as tetraethyleneglycol or hexaethyleneglycol, at either or both termini may also be substantially resistant to nuclease degradation.

Stabilization may also be a function of length or secondary structure. Unmethylated CpG-containing nucleic acid molecules that are tens to hundreds of kbs long are relatively resistant to in vivo degradation, particularly in a double-stranded closed-circular form (i.e., a plasmid). For shorter CpG-containing nucleic acid molecules, secondary structure may stabilize and increase their immunomodulatory effects. For example, if the 3' end of an oligonucleotide is complementary to an upstream region, it may fold back and form a stem loop structure such that it becomes stabilized thereby exhibiting increased activity.

For in vivo use, nucleic acids may also be associated with a molecule to form a "nucleic acid delivery complex" that results in higher affinity binding to target cell (e.g. B-cell, monocytic cell, macrophages, and natural killer (NK) cell) surfaces and/or in increased cellular uptake by target cells. Nucleic acids may be ionically or covalently associated with appropriate molecules using techniques known in the art. A variety of coupling or cross-linking agents may be used including for example protein A, carbodiimide, and N-succinimidyl-3-(2-pyridyldithio) propionate (SPDP). Nucleic acids may alternatively be encapsulated in liposomes or virosomes using standard techniques.

The immunomodulatory index of a particular CpG-containing nucleic acid molecule may be tested in various immune cell assays or in vivo assays known in the art or described herein. For example, the immunomodulatory or anti-autoimmune activity of a nucleic acid molecule may be assessed by its ability to treat, prevent, or reduce an autoimmune condition in a mammal. Exemplary immune assays are provided herein and in U.S. Pat. Nos. 6,194,388, 6,207,646, 6,214,806, 6,218,371, 6,239,116, 6,406,705, and 6,653,292, each of which is hereby incorporated by reference.

According to this invention, the mammal being treated is administered a therapeutically effective amount of the nucleic acid of the invention by any mode of administration, including for example, oral administration, transdermal (e.g., using a patch), injection (e.g., subcutaneous, intrvaveous, parenteral, intraperitoneal, intrathecal, etc,), intranasal, intrathecal, rectal, and mucosal. Desirably, the nucleic acids are administered systemically rather than locally. Suitable solid or liquid pharmaceutical preparation forms are, for example, granules, powders, tables, coated tablets, (micro) capsules, suppositories, syrups, emulsions, suspensions, creams, aerosols, drops, or injectable solution.

The pharmaceutical compositions of the invention may be prepared and administered in dose units. Solid dose units may be in the form of tablets, capsules, and suppositories but are typically formulated for intravenous administration. According to the invention, different daily doses may be required depending on the activity of the compound of the invention, the manner of administration, the nature and severity of the disease (e.g., rheumatoid arthritis) being treated, the age, and the body weight of the patient. If more than one injection is required, injections may be administered in bolus or as continuous infusion. Thus, higher or lower daily doses may be adjusted accordingly. The administration of the daily dose may be performed both by single administration in the form of an individual dose unit or several smaller dose units. Alternatively, multiple administrations of subdivided doses may be administered to the patient at specific intervals.

Secondary Agents

As described above, the methods of the invention may be used for the treatment of any autoimmune condition, including rheumatoid arthritis. If desired, one or more agents typically used to treat such conditions may be used in addition to the agent of the invention. Such agents include agents that are typically used to treat an autoimmune condition and thus are selected according to the autoimmune condition being treated. Secondary agents may be disease-modifying drugs or symptomatic agents (i.e. drugs that relieve condition-associated symptoms). Such agents include immunosuppressants (e.g, cyclosporine A, corticosteroids (prednisone), methotrexate, cyclophosphamide, and azathioprine), NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, steroidal anti-inflammatory agents (e.g., beclomethasone, flunisolide, budesonide, triamcinolone, prednisolone, dexamethasone, fluticasone, meclofenamate sodium, meloxicam, oxaprozin, sulindac, and tolmetin), COX-2 inhibitors (e.g., rofecoxib, celecoxib, valdecoxib, and lumiracoxib), inflammatory modulators (e.g., agents that modulate the expression of inflammatory cytokines (e.g., TNF-α or IL-1) or their receptors), agents that interfere with B cell action (e.g., anti-CD20 antibodies such as rituximab), biologics (e.g., inflixamab, adelimumab, etanercept, and CDP-870), non-steroidal calcineurin inhibitors (e.g., cyclosporine, tacrolimus, pimecrolimus, and ISAtx 247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine. Thus, in one embodiment, the invention features the combination of the agent of the invention with any of the foregoing agents, and methods of treating autoimmune conditions (e.g., rheumatoid arthritis) therewith.

If a second agent is used, it may be administered before, along with, or after the agent of the invention. If administered separately, the two agents may be administered within 1 hour, 2 hours, 4 hours, 6 hours, 12 hours, one day, two days, or one week of each other. Both agents may be administered by the same or different routes of administration and if desired, both agents may be admixed in a single pharmaceutical composition.

Production of Nucleic Acids

For use in the present invention, nucleic acid molecules may be synthesized de novo using any of a number of procedures well known in the art, such as the b-cyanoethyl phosphoramidite method (S. L. Beaucage and M. H. Caruthers, (1981) *Tet. Let.* 22:1859); nucleoside H-phosphonate method (Garegg et al., (1986) *Tet. Let.* 27: 4051-4054; Froehler et al., (1986) *Nucl. Acid. Res.* 14: 5399-5407; Garegg et al., (1986) *Tet. Let.* 27: 4055-4058, Gaffney et al., (1988) *Tet. Let.* 29:2619-2622). Alternatively, the nucleic acid molecules of the invention may be prepared from existing nucleic acid sequences (e.g. genomic or cDNA) using known techniques, such as those employing restriction enzymes, exonucleases, or endonucleases.

Screening Assays

The present invention also provides screening methods to identify additional compounds that can modulate the expression level or the biological activity of TLR-9. Using such agents as lead compounds, for example, the present screening methods also allow the identification of further novel, specific agents that function to treat, reduce, or prevent autoimmune conditions. The method of screening may involve high-throughput techniques.

A number of methods are available for carrying out such screening assays. According to one approach, candidate compounds are added at varying concentrations to the culture medium of cells expressing TLR-9. Gene expression of TLR-9 is then measured, for example, by standard Northern blot analysis (Ausubel et al., supra), using any appropriate fragment prepared from the nucleic acid molecule of TLR-9 as a hybridization probe or by real-time PCR with appropriate primers. The level of gene expression in the presence of the candidate compound is compared to the level measured in a control culture medium lacking the candidate molecule. If desired, the effect of candidate compounds may, in the alternative, be measured by means of the expression level of the TLR-9 polypeptide using the same general approach and standard immunological techniques, such as Western blotting or immunoprecipitation with an antibody specific to TLR-9, for example. For example, immunoassays may be used to detect or monitor the level of TLR-9. Polyclonal or monoclonal antibodies, which are capable of binding to TLR-9, may be used in any standard immunoassay format (e.g., ELISA or RIA assay) to measure the levels of TLR-9. TLR-9 may also be measured using mass spectroscopy, high performance liquid chromatography, spectrophotometric or fluorometric techniques, or combinations thereof.

The screening methods of the invention may be used to identify candidate compounds that modulate the expression level or biological activity of TLR-9. Such modulation is desirably at least 10%, 20%, 30%, 40%, 50%, 60%, 70%, 80%, 90%, 95%, or even 100% relative to an untreated control. Useful candidate compounds may also modulate TLR-9 level or activity by modulating the expression or activity of any of the molecules involved in TLR-9 signaling pathway. The biological activity of TLR-9 may be measured using any of the cell-based methods or in vivo methods standard in the art or described herein. For example, a candidate compound may be tested for its ability to modulate TLR-9 activity in cells that naturally express TLR-9, after transfection with a cDNA coding for TLR-9, or in cell-free solutions containing TLR-9. The effect of a candidate compound on the modulation of TLR-9 may be tested by radioactive and non-radioactive binding assays, competition assays, and receptor signaling assays.

As a specific example, mammalian cells (e.g., rodent cells) that express a nucleic acid encoding TLR-9 are cultured in the presence of a candidate compound (e.g., a nucleic acid molecule, peptide, polypeptide, synthetic organic molecule, naturally occurring organic molecule, or component thereof). Cells may either endogenously express TLR-9 or may alternatively be genetically engineered by any standard technique known in the art (e.g., transfection and viral infection) to overexpress TLR-9. The expression level of TLR-9 is measured in these cells by means of Western blot analysis and subsequently compared to the level of expression of the same protein in control cells that have not been contacted by the candidate compound. A compound which promotes a modulation in the level of TLR-9 activity as a result of modulating its synthesis or biological activity is also considered useful in the invention. A compound that modulates TLR-9 activity or levels is useful according to the present invention.

Alternatively, or in addition, candidate compounds may be screened for those which specifically bind to and thereby modulate TLR-9 activity or levels. The efficacy of such a candidate compound is dependent upon its ability to interact with TLR-9. Such an interaction can be readily assayed using any number of standard binding techniques and functional assays (e.g., those described in Ausubel et al., supra). For example, a candidate compound may be tested in vitro for interaction and binding with TLR-9 and its ability to modulate TLR-9 activity or levels may be assayed by any standard assays (e.g., those described herein).

In one particular example, a candidate compound that binds to TLR-9 may be identified using a chromatography-based technique. For example, a recombinant TLR-9 may be purified by standard techniques from cells engineered to express TLR-9 (e.g., those described above) and may be immobilized on a column. Alternatively, the naturally-occurring TLR-9 may be immobilized on a column. A solution of candidate compounds is then passed through the column, and a compound specific for TLR-9 is identified on the basis of its ability to bind to TLR-9 and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). Compounds which are identified as binding to TLR-9 with an affinity constant less than or equal to 10 mM are considered particularly useful in the invention.

Screening for new autoimmune condition therapeutics and optimization of lead compounds may be assessed, for example, by assessing their ability to function as anti-autoimmune agents (e.g., as described herein). Compounds isolated by this approach may also be used, for example, as therapeutics to treat, reduce, or prevent autoimmune conditions. In this regard, the anti-autoimmune efficacy of any of the candidate compounds identified by the present screening methods may be tested using any of the autoimmune models described herein or known in the art.

In addition to nucleic acid molecules that contain unmethylated CpG sequences (as described above), potential therapeutic agents include organic molecules, peptides, peptide mimetics, polypeptides, and antibodies that bind to a nucleic acid sequence or polypeptide that encodes TLR-9 and thereby modulate their activity. Potential anti-autoimmune agents also include small molecules that bind to and occupy the binding site of such polypeptides thereby preventing or enhancing binding to cellular binding molecules, such that normal biological activity is modulated. Other potential anti-autoimmune agents may also include antisense molecules.

Test Compounds and Extracts

In general, compounds capable of treating, reducing, or preventing autoimmune conditions are identified from large libraries of both natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-hypertensive activity should be employed whenever possible.

When a crude extract is found to have an anti-autoimmune activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having anti-autoimmune activity. Methods of fractionation and purification of such heterogenous extracts are known in the art. If desired, compounds shown to be useful agents for the treatment of pain are chemically modified according to methods known in the art.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating or reducing inflammatory arthritis, type I diabetes, inflammatory bowel disease, multiple sclerosis, myasthenia gravis, or systemic lupus erythematosus (SLE) in a mammal in need thereof by administering systemically to said mammal a therapeutically effective amount of a pharmaceutical composition comprising a polynucleotide comprising the sequence 5' TCC ATG ACG TTC CTG ACG TT 3' (ODN 1826; SEQ ID NO: 3) or 5' TCC ATG ACG TTC CTG ATG CT 3' (ODN 1668; SEQ ID NO:5).

2. The method of claim 1, wherein said polynucleotide comprises at least one unmethylated CpG dinucleotide (CpG ODN).

3. The method of claim 1, wherein said polynucleotide is single-stranded.

4. The method of claim 1, wherein said polynucleotide is DNA or RNA.

5. The method of claim 1, wherein said polynucleotide comprises at least one nucleotide having a phosphate backbone modification.

6. The method of claim 5, wherein said phosphate backbone modification is a phosphothioate or phosphorodithioate modification.

7. The method of claim 5, wherein said phosphate backbone modification is on the 5' inter-nucleotide linkages.

8. The method of claim 5, wherein said phosphate backbone modification is on the 3' inter-nucleotide linkages.

9. The method of claim 1, wherein said polynucleotide comprises 20 to 100 nucleotides.

10. The method of claim 9, wherein said polynucleotide comprises 20 to 30 nucleotides.

11. The method of claim 1, wherein said polynucleotide modulates the activity of B cells, dendritic cells, monocytes, macrophages, or a combination thereof.

12. The method of claim 1, wherein said polynucleotide modulates the levels of TNF-α, IL-12, or both.

13. The method of claim 1, wherein said mammal has inflammatory arthritis.

14. The method of claim 13, wherein said inflammatory arthritis is rheumatoid arthritis, juvenile arthritis, or psoriatic arthritis.

15. The method of claim 1, further comprising administering a second therapeutic agent.

16. The method of claim 15, wherein said second therapeutic agent is selected from the group consisting of immunosuppressants, NSAIDs, COX-2 inhibitors, biologics, non-steroidal calcineurin inhibitors, steroidal anti-inflammatory agents, 5-amino salicylic acid, DMARDs, hydroxychloroquine sulfate, inflammatory modulators, agents that interfere with B cell action, and penicillamine.

17. The method of claim 1, wherein said mammal is a human, dog, cat, horse, cow, pig, sheep, goat, or monkey.

18. The method of claim 17, wherein said mammal is a human.

19. The method of claim 1, wherein said polynucleotide is double-stranded.

20. The method of claim 14, wherein said inflammatory arthritis is rheumatic arthritis.

21. The method of claim 14, wherein said inflammatory arthritis is psoriatic arthritis.

22. The method of claim 14, wherein said inflammatory arthritis is juvenile arthritis.

23. The method of claim 13, wherein said polynucleotide comprises the sequence of ODN 1826.

24. The method of claim 23, wherein said polynucleotide consists of the sequence of ODN 1826.

25. The method of claim 13, wherein said polynucleotide comprises the sequence of ODN 1668.

26. The method of claim 25, wherein said polynucleotide consists of the sequence of ODN 1668.

* * * * *

UNITED STATES PATENT AND TRADEMARK OFFICE
CERTIFICATE OF CORRECTION

PATENT NO. : 7,973,016 B2  Page 1 of 1
APPLICATION NO. : 10/586401
DATED : July 5, 2011
INVENTOR(S) : Diane J. Mathis, Christophe O. Benoist and Hsin-Jung Wu It is certified that error appears in the above-identified patent and that said Letters Patent is hereby corrected as shown below:

In the title page, section (73), please correct the spelling of the Assignee name as shown below.

"Joslin Diebetes Center, Inc., Boston, Massachusetts" should read instead

--Joslin Diabetes Center, Inc., Boston, Massachusetts--

Signed and Sealed this
Twenty-seventh Day of September, 2011

David J. Kappos
*Director of the United States Patent and Trademark Office*

SEQUENCE LISTING

<160> NUMBER OF SEQ ID NOS: 5

<210> SEQ ID NO 1
<211> LENGTH: 6
<212> TYPE: DNA
<213> ORGANISM: Artificial Sequence
<220> FEATURE:
<223> OTHER INFORMATION: synthetic

<400> SEQUENCE: 1 gacgtt                                                                  6

<210> SEQ ID NO 2
<211> LENGTH: 6
<212> TYPE: DNA
<213> ORGANISM: Artificial Sequence
<220> FEATURE:
<223> OTHER INFORMATION: synthetic

<400> SEQUENCE: 2 gtcgtt                                                                  6

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3

```
tccatgacgt tcctgacgtt                                              20

<210> SEQ ID NO 4
<211> LENGTH: 18
<212> TYPE: DNA
<213> ORGANISM: Artificial Sequence
<220> FEATURE:
<223> OTHER INFORMATION: synthetic

<400> SEQUENCE: 4
tctcccagcg tgcgccat                                                18

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
tccatgacgt tcctgatgct                                              20
```